United States Patent
Kulkarni

(10) Patent No.: US 9,401,016 B2
(45) Date of Patent: Jul. 26, 2016

(54) USING HIGH RESOLUTION FULL DIE IMAGE DATA FOR INSPECTION

(71) Applicant: KLA-Tencor Corporation, Milpitas, CA (US)

(72) Inventor: Ashok V. Kulkarni, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/707,592

(22) Filed: May 8, 2015

(65) Prior Publication Data

US 2015/0324965 A1  Nov. 12, 2015

Related U.S. Application Data

(60) Provisional application No. 61/991,892, filed on May 12, 2014.

(51) Int. Cl.
| | |
|---|---|
| G06K 9/00 | (2006.01) |
| G06T 7/00 | (2006.01) |
| G06T 7/60 | (2006.01) |
| G06F 17/50 | (2006.01) |
| G01N 21/88 | (2006.01) |
| G01B 21/16 | (2006.01) |
| H01L 21/66 | (2006.01) |
| H01L 21/67 | (2006.01) |

(52) U.S. Cl.
CPC .............. *G06T 7/001* (2013.01); *G01B 21/16* (2013.01); *G01N 21/8851* (2013.01); *G06F 17/5045* (2013.01); *G06T 7/0044* (2013.01); *G06T 7/60* (2013.01); *H01L 21/67288* (2013.01); *H01L 22/12* (2013.01); *G01N 2201/10* (2013.01); *G01N 2201/12* (2013.01); *G06T 2207/30148* (2013.01)

(58) Field of Classification Search
CPC ............... G06T 7/0006; G06T 2207/20076; G06T 7/0008; G06T 2207/30148; G06T 7/001; G06T 2200/28; G06T 7/60; G06T 7/0044; G03F 1/84; G01B 21/16; H01L 22/12; H01L 21/67288; G01N 21/8851; G06F 17/5045
See application file for complete search history.

(56) References Cited

U.S. PATENT DOCUMENTS

| | | | |
|---|---|---|---|
| 6,091,846 A * | 7/2000 | Lin | G01N 21/9501 257/E21.525 |
| 6,902,855 B2 | 6/2005 | Peterson et al. | |
| 7,512,508 B2 * | 3/2009 | Rajski | G01R 31/01 438/14 |
| 7,570,800 B2 | 8/2009 | Lin et al. | |

(Continued)

OTHER PUBLICATIONS

International Search Report for PCT/US2015/030145 mailed Aug. 26, 2015.

*Primary Examiner* — Brian Le
(74) *Attorney, Agent, or Firm* — Ann Marie Mewherter

(57) ABSTRACT

Methods and systems for determining a position of inspection data with respect to a stored high resolution die image are provided. One method includes aligning data acquired by an inspection system for alignment sites on a wafer with data for predetermined alignment sites. The predetermined alignment sites have a predetermined position in die image space of a stored high resolution die image for the wafer. The method also includes determining positions of the alignment sites in the die image space based on the predetermined positions of the predetermined alignment sites in the die image space. In addition, the method includes determining a position of inspection data acquired for the wafer by the inspection system in the die image space based on the positions of the alignment sites in the die image space.

89 Claims, 1 Drawing Sheet

(56) References Cited

U.S. PATENT DOCUMENTS

| | | |
|---|---|---|
| 7,676,077 B2 | 3/2010 | Kulkarni et al. |
| 7,729,529 B2 | 6/2010 | Wu et al. |
| 8,126,255 B2 | 2/2012 | Bhaskar et al. |
| 9,092,846 B2 | 7/2015 | Wu et al. |
| 9,098,891 B2 | 8/2015 | Kulkarni et al. |
| 9,171,364 B2 | 10/2015 | Wu et al. |
| 9,189,844 B2 | 11/2015 | Wu et al. |
| 2004/0022429 A1* | 2/2004 | Suzuki ............ G06T 7/001 382/145 |
| 2005/0033528 A1* | 2/2005 | Toth ............ G01N 21/9501 702/35 |
| 2009/0078868 A1 | 3/2009 | De Jonge |
| 2011/0170091 A1 | 7/2011 | Chang et al. |
| 2011/0286656 A1 | 11/2011 | Kulkarni et al. |
| 2012/0319246 A1 | 12/2012 | Tan et al. |
| 2013/0064442 A1* | 3/2013 | Chang ............ G06T 7/001 382/149 |
| 2013/0198697 A1* | 8/2013 | Hotzel ............ G03F 1/24 716/51 |
| 2013/0279792 A1 | 10/2013 | Hess et al. |
| 2014/0105482 A1 | 4/2014 | Wu et al. |
| 2014/0301629 A1 | 10/2014 | Ramachandran |
| 2015/0015870 A1* | 1/2015 | Lin ............ H01L 22/12 356/72 |

* cited by examiner

USING HIGH RESOLUTION FULL DIE IMAGE DATA FOR INSPECTION

BACKGROUND OF THE INVENTION

1. Field of the Invention

This invention generally relates to methods and systems for determining a position of inspection data with respect to a stored high resolution die image.

2. Description of the Related Art

The following description and examples are not admitted to be prior art by virtue of their inclusion in this section.

Semiconductor manufacturing involves a large and complex set of imaging, etching, deposition and planarization processes in order to construct sub-micron (down to a few tens of nanometers) geometrical patterns on a silicon substrate. After a process has been performed to at least partially construct the patterns on the silicon substrate, the substrate must be inspected to determine if there are defects in the patterns or on the substrate. There are a number of different methods and systems that are used to inspect such substrates for defects. The type of method or system that is used for any particular substrate that has undergone any particular fabrication process may be selected based on characteristics of the substrate as well as the defects that are to be detected on the substrate.

Some inspection systems and methods make use of the design data for the substrates during inspection or to set up inspection. For example, the design layout of the die being formed on such substrates is often used to identify critical regions (such as areas of high geometry density) and other so-called "hot spots" where defects can manifest themselves. By separating critical from non-critical regions, a more sensitive inspection can be performed in the critical areas and a less sensitive inspection in the less critical areas. U.S. Pat. No. 7,676,077 issued on Mar. 9, 2010 to Kulkarni et al., which is incorporated by reference as if fully set forth herein, describes this approach.

The design layout may also be used to classify defects detected on wafers. For example, a design-based classification (DBC) approach may use a post-processing approach to bin/classify defects found by an inspection tool using design context around each detected defect. Thus, determining critical areas and classifying defects based on design data provide a "front-end" and "back-end" approach to detecting and filtering of defects in order to flag systematic as well as random yield-relevant defects. Therefore, the approaches described above require design data to be available. However, in many circumstances, the design information may not be readily available.

Another approach, commonly referred to as target-based inspection (TBI) seeks to utilize a priori locations or hot spots that are known to the user. TBI uses an optical template around these areas of interest to mark all such regions of a die, which are then inspected at a higher sensitivity. Therefore, TBI is restricted to only those a priori locations where it is known that defects are likely to occur. In many instances, this data is either incomplete or unknown.

Accordingly, it would be advantageous to develop methods and/or systems for wafer inspection-related applications that do not have one or more of the disadvantages described above.

SUMMARY OF THE INVENTION

The following description of various embodiments is not to be construed in any way as limiting the subject matter of the appended claims.

One embodiment relates to a computer-implemented method for determining a position of inspection data with respect to a stored high resolution die image. The method includes aligning data acquired by an inspection system for alignment sites on a wafer with data for predetermined alignment sites. The predetermined alignment sites have predetermined positions in die image space of a stored high resolution die image for the wafer. The method also includes determining positions of the alignment sites in the die image space based on the predetermined positions of the predetermined alignment sites in the die image space. In addition, the method includes determining a position of inspection data acquired for the wafer by the inspection system in the die image space based on the positions of the alignment sites in the die image space. Aligning the data, determining the positions of the alignment sites, and determining the position of the inspection data are performed by a computer system.

The computer-implemented method described above may be performed as described further herein. In addition, the computer-implemented method described above may include any other step(s) of any other method(s) described herein. Furthermore, the computer-implemented method described above may be performed by any of the systems described herein.

Another embodiment relates to a system configured to determine a position of inspection data with respect to a stored high resolution die image. The system includes a storage medium that includes a stored high resolution die image for a wafer. The system also includes a processor coupled to the storage medium. The processor is configured for performing the steps of the computer-implemented method described above. The system may be further configured as described herein.

An additional embodiment relates to another system configured to determine a position of inspection data with respect to a stored high resolution die image. The system includes an inspection system configured to acquire data for alignment sites on a wafer and inspection data for the wafer. The system also includes the storage medium described above and the processor described above that is, in this embodiment, also coupled to the inspection system. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
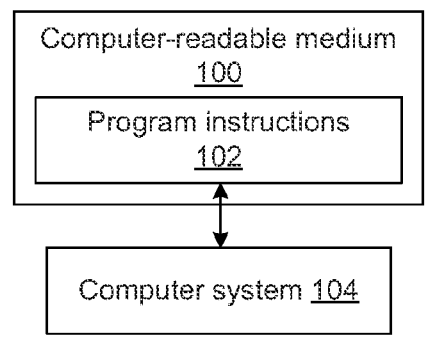
FIG. 1 is a block diagram illustrating one embodiment of a non-transitory computer-readable medium storing program instructions executable on a computer system for performing one or more of the computer-implemented methods described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

In general, the embodiments described herein relate to methods and systems for utilizing high resolution full die image data in combination with inspection data. For example, one embodiment relates to a computer-implemented method for determining a position of inspection data with respect to a stored high resolution die image. The method includes aligning data acquired by an inspection system for alignment sites on a wafer with data for predetermined alignment sites. Aligning the data for the alignment sites to the data for the predetermined alignment sites may be performed using any suitable alignment method(s) and/or alignment algorithm(s) known in the art.

The predetermined alignment sites have predetermined positions in die image space of a stored high resolution die image for the wafer. The predetermined alignment sites may be selected in a number of different ways as described further herein. The predetermined positions in the die image space may be coordinates with respect to some point (e.g., the origin) in the die image. In this manner, the predetermined positions in the die image space may be expressed as die image space coordinates.

In one embodiment, the stored high resolution die image is a stored high resolution image of an entirety of the die. For example, the stored high resolution die image may be acquired and stored as described herein for an entire die. Therefore, even though only portions of the stored die image may be needed for some of the steps described herein (e.g., alignment), the entire die image may be available for use in any of the steps described herein. A "high resolution" die image as that term is used herein is intended to refer to an image in which all of the features formed on a wafer are resolved.

Therefore, the "resolution" of the high resolution die image should be equal to or greater than the smallest feature formed on the wafer. In other words, if the smallest feature formed in a die on the wafer is (say) 10 nm, then a "high resolution" die image for that wafer should be formed with an imaging system capable of a resolution of at least 10 nm.

In this manner, the features in the high resolution die image will accurately represent the design for the wafer such that the image could be used to determine substantially accurate information about the design for the wafer.

In another embodiment, the method includes acquiring the high resolution die image for the wafer by scanning a die on the wafer or another wafer with an electron-beam based imaging system and storing the acquired high resolution die image in a storage medium. For example, a single die on a sample semiconductor wafer may be scanned using a high resolution imaging tool such as an electron beam inspection (EBI) system, including such systems that are commercially available from KLA-Tencor, Milpitas, Calif., or using a step-and-repeat electron beam review (EBR) system such as the 7100 series system that is commercially available from KLA-Tencor or any other suitable system. These steps may be performed during inspection recipe setup. A "recipe" may be generally defined as a set of instructions for carrying out a process such as inspection. The high resolution die image may be stored in any of the storage media described herein.

In some embodiments, design data for the wafer is not available for use in the method. For example, in many circumstances in which parameter(s) are being determined for wafer inspection, the design information may not be readily available. In such cases, the embodiments described herein may be used, as described further herein, to identify and separate critical regions on the die from the less critical regions using a high resolution imaging tool such as a scanning electron microscope (SEM) with image processing and pattern recognition techniques. In this case, one can regard the SEM image as a proxy for the design since it has the resolution to show the geometries on the wafer in sufficient detail to allow for separating critical and noncritical regions of the die. In this manner, the stored die image can serve as a proxy for design context and can be used as described further herein for aligning to "design" and possibly for defining critical areas (different sensitivity regions) as well as to classify (bin) defects based on "design" context.

The terms "design" and "design data" as used herein generally refer to the physical design (layout) of an IC and data derived from the physical design through complex simulation or simple geometric and Boolean operations. The design may be stored in a data structure such as a GDS file, any other standard machine-readable file, any other suitable file known in the art, and a design database. A GDSII file is one of a class of files used for the representation of design layout data. Other examples of such files include GL1 and OASIS files. The design used in the embodiments described herein may be stored in any of this entire class of files irrespective of data structure configuration, storage format, or storage mechanism. In addition, the design data can be standard cell library data, integrated layout data, design data for one or more layers, derivatives of the design data, and full or partial chip design data.

In general, however, the design information or data cannot be generated by imaging a wafer with a wafer inspection system. For example, wafer inspection systems are generally not capable of generating images of the design patterns formed on wafers with sufficient resolution such that the images could be used to determine information about the design for the wafer. Therefore, in general, the design information or design data cannot be generated using a wafer inspection system. In addition, the "design" and "design data" described herein refers to information and data that is generated by a semiconductor device designer in a design process and is therefore available for use in the embodiments described herein well in advance of printing of the design on any physical wafers.

A number of different ways that the predetermined alignment targets can be selected are described herein. In general, selecting the predetermined alignment targets may include, in each die-swath in a scan, searching for a set of potential alignment targets using some criteria described further herein. The corresponding locations of these targets can then be identified in the stored die image. For example, the method may include identifying alignment targets on the wafer and storing their locations and offsets with respect to the die image origin as alignment target information. For targets that have relatively good alignment scores and quality (i.e., magnitude and sharpness of peaks in a cross-correlation surface resulting from aligning the wafer image patch with the stored image patch), these locations and their offsets with respect to the die image origin, as well as the image patches may be stored as part of the inspection recipe for use during future inspections of this layer. In this manner, data for and/or images of the predetermined alignment sites (or indices that refer to this data) may be stored in the recipe for the inspection process, and the alignment data may be used each time the inspection system inspects a wafer of this particular device and layer. The predetermined alignment sites and information for those sites may also be selected and stored as described in U.S. Pat. No. 7,676,077 issued on Mar. 9, 2010 to Kulkarni et al., which is incorporated by reference as if fully set forth herein. These steps may be performed during inspection recipe setup.

In some embodiments, the method includes selecting the predetermined alignment sites by pre-processing the stored high resolution die image to select predetermined alignment sites that are compatible with the inspection system and an inspection process to be used by the inspection system for the wafer. Selecting the predetermined alignment sites may include pre-processing the stored die image to select predetermined alignment sites that are compatible with the inspection process and system in a number of different ways. For example, the stored die image may be processed to identify patterned features included in the stored die image that are unique in some way with respect to surrounding patterned features. In this manner, the patterned features can be uniquely identified in the stored die image. The identified patterned features may then be analyzed to determine which of the identified patterned features can be imaged by the inspection system with sufficient resolution so that the images for the patterned features generated by the inspection system can be aligned substantially accurately to images for the patterned features in the stored die image. For instance, if some of the identified patterned features will not be resolved in images generated by the inspection system, they may be eliminated as potential alignment sites for use in the embodiments described herein. In this manner, patterned features in the stored high resolution die image that are unique enough to be useful as predetermined alignment sites and that can be adequately imaged by the inspection system can be selected for use as the predetermined alignment sites.

In one embodiment, the method includes selecting the predetermined alignment sites based on information about one or more optical modes and pixel size to be used by the inspection system for inspection of the wafer. In one example, during setup of an inspection process performed by an inspection system, information about parameters of the inspection system such as wafer swathing information, inspection system model number, optical mode(s) to be used for inspection, and pixel size, in addition to the stored die image may be used to select the predetermined alignment sites. The predetermined alignment sites may also be selected based on one or more attributes of the wafer to be inspected. In this manner, information about the imaging ability of the inspection system (e.g., as defined by the optical mode(s), pixel size, etc.) that will be used for wafer inspection can be used to determine which patterned features in the stored die image will be suitable for use as the predetermined alignment sites. For example, based on information about the imaging capability of the inspection system, any patterned features in the stored die image that are expected to be resolved in images produced by the inspection system may be identified as potential alignment sites. Characteristics of the identified potential alignment sites (e.g., position in the stored die image, uniqueness of the geometry of the potential alignment sites, etc.) may then be used to make final selections for the predetermined alignment sites.

In some embodiments, the data acquired for the alignment sites on the wafer and the inspection data, described further herein, are acquired with two or more optical modes on the inspection system. For example, if a wafer is scanned in multiple imaging modes, which might be simultaneously performed or performed in multiple scans of the wafer, the embodiments described herein can be applied as long as one can find alignment targets in the different imaging modes to align with the stored die image as described further herein. An "optical mode" or "imaging mode" as that term is used herein generally refers to a set of optical parameters that in combination can be used to acquire images or other similar data for a wafer. Therefore, an "optical mode" or "imaging mode" may be defined by a number of illumination parameters such as angle of incidence, polarization, wavelength, etc. as well as a number of detection parameters such as angle of collection/detection, polarization, wavelength, etc. As such, different optical modes or different imaging modes may be different in value(s) for one or more such parameters.

In one such embodiment, the alignment sites used for a first of the two or more optical modes are different from the alignment sites used for a second of the two or more optical modes. In this manner, different alignment sites may be used for different optical modes. For example, one alignment site may be particularly useful for alignment for one optical mode, but not useful for alignment in another optical mode. Therefore, a different alignment site that is more useful for alignment in the other optical mode may be identified and used for that mode. However, if an alignment site can be identified that is sufficiently useful for alignment in more than one optical mode, that alignment site can be used for alignment purposes in each of those more than one optical mode. In either case, alignment sites can be selected for one or more optical modes according to any of the embodiments described herein.

In another such embodiment, the data for the predetermined alignment sites used for a first of the two or more optical modes is different than the data for the predetermined alignment sites used for a second of the two or more optical modes. For example, if different alignment sites are used for different optical modes as described further above, then different predetermined alignment sites and their corresponding data would be used for the different optical modes as well.

In one embodiment, the data for the alignment sites on the wafer includes scanned images, and the data for the predetermined alignment sites includes high resolution image data from the stored high resolution die image. For example, the scanned images may be images acquired by the inspection system during an inspection process performed on the wafer. The high resolution image data used for the predetermined alignment sites may include any suitable portion of the stored high resolution image data surrounding and near the predetermined alignment sites. The scanned images used for the alignment sites may be acquired in the same scan as the inspection data (i.e., using the optical mode(s) that is/are used for inspecting the wafer) or a different scan than that used to generate the inspection data (e.g., if the alignment sites are not imaged using the inspection optical mode(s) such that they can be aligned to the high resolution image data for the predetermined alignment sites). In that case, the alignment of the alignment sites and the predetermined alignment sites may be performed using one optical mode of the inspection system and then that alignment may be translated to another optical mode of the inspection system (e.g., by aligning both the alignment site data acquired using one or more inspection optical modes and the predetermined alignment site data to the alignment site data acquired using a different optical mode).

In another embodiment, the data for the alignment sites on the wafer includes scanned images, and the data for the predetermined alignment sites includes image clips. Data or images for the predetermined alignment sites that may be used in the methods described herein include stored die image clips (the term "clip" as used herein refers to a relatively small portion of the entire stored high resolution die image) and images generated by an inspection system that have been aligned to a stored high resolution die image.

In an additional embodiment, the method includes extracting high resolution die image clips for the predetermined alignment sites from the stored high resolution die image and storing the extracted image clips in a file that is used by the inspection system for inspection of the wafer. The high resolution die image clips may be extracted from the entire stored high resolution die image in any suitable manner. In addition, the extracted image clips may be stored in the file that is used by the inspection system for inspection in any suitable manner. In this manner, the file that is used by the inspection system for alignment may not include the entire stored high resolution die image thereby reducing the data handling capabilities required during inspection. However, the entire stored high resolution die image may also be available for use during inspection (e.g., in another file available for use by the inspection system) such that all of the stored high resolution die image data can be accessed as necessary.

In a further embodiment, the method includes scanning the wafer using the best imaging mode of the inspection system for inspection to select suitable predetermined alignment sites and determining positions of the selected predetermined alignment sites based on images produced by the scanning and the stored high resolution die image. The alignment site selection step may also be performed based on the various imaging modes that may be used to inspect the wafer. For instance, the inspection system may be configured to use more than one optical imaging mode for inspection such as bright field (BF) mode, dark field (DF) mode, Edge Contrast (which is a trademark of KLA-Tencor) mode, various aperture modes, and/or an electron beam imaging mode. Edge Contrast (EC) inspection is generally performed using a circular symmetric illumination aperture with a complementary imaging aperture. The best imaging mode for inspection of a particular layer on a wafer is the imaging mode that maximizes the defect signal-to-noise ratio (S/N), and the best imaging mode may vary with the layer type. In addition, the inspection system may be configured to inspect a wafer using more than one imaging mode simultaneously or sequentially. Since alignment site image or data acquisition performed during wafer inspection uses the best imaging mode for wafer inspection, the alignment site selection preferably uses that mode to select appropriate alignment sites and alignment features.

However, to precisely determine the positions of the selected predetermined alignment sites in the die image space, the inspection system may be used to acquire high resolution images of the selected predetermined alignment sites that are then aligned to the corresponding portions of the stored high resolution die image to thereby determine the positions of the selected predetermined alignment sites in die image space. In this manner, the images acquired using the best mode for matching with the stored die image may be aligned to the stored die image. Using the (x, y) positions of the selected alignment sites in the die image space determined by aligning the images acquired using the best mode for matching to the stored die image, these x and y positions can be associated with the patch images acquired using the best mode for inspection. If there is some fixed offset between the images gathered for the same site in the different modes (inspection mode and best mode for matching to the stored die image), this offset can be measured and/or corrected at the start of (or before) inspection using a suitable calibration target.

In one such embodiment, the method may include off-line alignment of different images of the predetermined alignment sites to determine mapping (i.e., to determine the positions of individual pixels of the optical or electron beam image in die image space). For example, after selecting the predetermined alignment sites and acquiring images of those sites on the wafer using the imaging mode that can provide the best images for matching with the stored die image, the different images may then be aligned to each other using any appropriate method and/or algorithm known in the art.

Alternatively, the portions of the stored high resolution die image corresponding to selected predetermined alignment sites may be used to simulate images of the predetermined alignment sites that would be formed by the inspection system using the mode used for selection of the predetermined alignment sites. The simulated images can then be aligned to the images acquired by the inspection system for the selected predetermined alignment sites to thereby determine the positions of the alignment sites on the wafer in die image space. Obtaining a simulated image having suitable quality for alignment of the simulated image and the optical image may be difficult for all imaging modes. However, a best match of the simulated image and the optical image may be obtained for a particular imaging mode (e.g., BF mode). Therefore, the method may include scanning the wafer using the best imaging mode for inspection to select suitable predetermined alignment sites. The method may also include revisiting the selected predetermined alignment sites on the wafer using the inspection system to acquire optical patch images using the mode that provides an image that can best be matched to the simulated image.

In one embodiment, the method includes selecting the predetermined alignment sites by scanning a die row on a wafer using the inspection system and processing each frame of a die to identify unique alignment sites. The term "frame" is generally defined herein as data or an image for a portion of a die in a swath of inspection data or images acquired during scanning of the wafer. Each swath may be acquired as a stream of pixels of some height H (in y) as the inspection system scans (in x) across the die in a row or column on the wafer. Processing the frames may include determining the x and y gradients of features in the frames and selecting one or more features that have a relatively strong gradient in the x and/or y directions for use in the predetermined alignment sites. The method may also include performing a cross-correlation of a frame and a patch image containing such a feature to determine if only one relatively strong peak of the gradient(s) is located within a predetermined search range. In this manner, alignment features that are unique within a pattern search window may be identified and selected for the predetermined alignment sites. The method may also include displaying one or more potential alignment sites (e.g., optical or electron beam images for the potential alignment sites) identified by the method and allowing a user to select one or more suitable alignment sites distributed over the die at a predetermined minimum interval distance.

In some embodiments, the method includes selecting the predetermined alignment sites from the stored high resolution die image for the wafer such that there is at least one predetermined alignment site in each of multiple swaths of the inspection data. In another embodiment, the method includes selecting the predetermined alignment sites by dividing the stored high resolution die image into portions that correspond to each of multiple swaths of the inspection data and searching the stored high resolution die image to identify and select at least one of the predetermined alignment sites in each of the multiple swaths. For example, the parameters of the inspection process that will be used for inspection of the wafer can be used to determine how the dies on the wafer will be divided up into swaths of inspection data. That information can then be used to determine the corresponding division of the stored high resolution die image into swaths. Different swaths of the stored high resolution die image may then be processed separately such that at least one predetermined alignment site is selected in each of the swaths. Such selection in each of the swaths may be performed according to any embodiments described herein. In this manner, the predetermined alignment sites used for an inspection process may include a set of predetermined alignment sites that includes at least one predetermined alignment site in each swath of inspection data generated for the wafer. As such, each swath of the inspection data can be individually aligned to the stored high resolution die image.

In some embodiments, the alignment sites include more than one alignment site in each of multiple swaths of the inspection data. For example, the alignment sites may be selected as described above such that more than one alignment site is included in each swath of inspection data. In another such embodiment, the alignment sites include more than one alignment site in each of multiple swaths of the inspection data to correct scaling errors. In some embodiments, aligning the inspection system to the alignment sites is performed to correct stage positional accuracy, rotational errors, x and y translational errors, or some combination thereof in the inspection system. For example, after the inspection system has been aligned to the alignment sites, stage positional accuracy, any rotational errors, x and y translational errors, magnification (scaling) errors, or some combination thereof may be corrected. This correction may take place during the inspection process or may be performed post-process (i.e., performed after inspection results have been produced). The correction may be based, at least in part, on a comparison of the coordinates for the alignment sites reported by the inspection system and reference coordinates for the same alignment sites. In other words, the alignment sites selected as described herein may be used to not only align the inspection data to the stored high resolution die image but may also be used to align the inspection system to wafer space coordinates.

In a further embodiment, the predetermined alignment sites are selected at a predetermined frequency across a die on the wafer. In another embodiment, the predetermined alignment sites are distributed over a die on the wafer at a predetermined minimum interval distance. For example, the predetermined alignment sites may be selected at a frequency or minimum interval distance based on a priori knowledge about the scanning capability of the inspection system to be used for inspection of the wafer. In one such example, for an inspection system that is known to drift significantly during acquisition of a swath of inspection data, the predetermined alignment sites may be selected at a relatively high frequency across the die and/or at relatively small minimum interval distances. In this manner, the alignment sites can be used to substantially accurately align all of the inspection data to the stored high resolution die image regardless of the marginalities of the inspection system.

In one embodiment, the method includes selecting the predetermined alignment sites to include a set of alignment features that in combination provide sufficient alignment information for determining the positions of the alignment sites, as described further herein. For example, each of the predetermined alignment sites may include one or more alignment features, and those one or more alignment features may be selected as described herein so that they provide sufficient information for performing steps of the method described herein.

In a further embodiment, the aligning step is performed before defect detection for the wafer. For example, aligning the data for the alignment sites to the data for the predetermined alignment sites may be performed during or after acquisition of the inspection data and before defect detection is performed using the inspection data. In this manner, the inspection data may be aligned to the stored high resolution die image prior to defect detection, which may be advantageous in some embodiments described further herein such as those in which the stored high resolution die image or information from that die image is used for the defect detection.

In some embodiments, the inspection system is configured to use a BF mode for inspection of the wafer. In another embodiment, the inspection system is configured to use a dark field DF mode for inspection of the wafer. In a further embodiment, the inspection system is configured to use an electron beam imaging mode for inspection of the wafer. Such inspection systems may be configured as described further herein. In addition, the embodiments described herein can be configured for use with any inspection system configuration and optical or electron beam modes.

The method also includes determining positions of the alignment sites in the die image space based on the predetermined positions of the predetermined alignment sites in the die image space. For instance, since the (x, y) positions of the predetermined alignment sites with respect to the die image coordinates (i.e., in the die image space) have been determined and the data for the predetermined alignment sites has been aligned to the data for the alignment sites, the absolute locations of the live pixel coordinates of the alignment sites on the wafer can be determined in die image space. Determining the positions of the alignment sites on the wafer in die image space may be performed before inspection of the wafer or subsequent to acquisition of the inspection data for the wafer.

The method also includes determining a position of inspection data acquired for the wafer by the inspection system in the die image space based on the positions of the alignment sites in the die image space. The inspection data for which the position in die image space is determined may include any data (e.g., image data) acquired for the wafer by the inspection system during inspection. In addition, the position of the inspection data may be determined for some or all of the data acquired by the inspection system during inspection of the wafer. For example, the position of the inspection data may be determined only for inspection data acquired for care areas on the wafer.

In one embodiment, after aligning the portions of the raw data stream corresponding to the alignment sites on the wafer to the data for the predetermined alignment sites as described above, the method may include measuring the coordinate offset between the inspection data stream and the stored die image to within sub-pixel accuracy. In addition, the coordinate errors between the live inspection data and the stored die image may be corrected by shifting the raw inspection data image with respect to the stored die images for the predetermined alignment sites so that the alignment sites on the wafer are substantially exactly aligned to the predetermined alignment sites for all points across the die. One significant advantage of the methods and systems described herein is that the position of the inspection data in the die image space can be determined with sub-pixel accuracy. In this manner, the care and do not care areas on the wafer may be determined as described further herein with relatively high precision at sub-100 nm accuracy.

In a different embodiment, the data for the predetermined alignment sites may be used to determine a two-dimensional mapping transform that can be used to map the live image pixel space to die image space. For instance, the method may include correlating downloaded predetermined alignment site patch images (acquired during setup of the inspection process) with the live image data over a predetermined search range and determining the offset between the downloaded and live images. The method may also include determining the correspondence between the live image pixel positions and the die image coordinates using this offset since the (x, y) positions of the predetermined alignment sites in die image space were determined during setup. The method may then include determining a two-dimensional function for mapping the live pixel coordinate space to the die image space using the correspondence between the live image pixel positions and the die image coordinates.

In one such example, using a suitable polynomial fit of a grid of alignment sites to the absolute coordinates in die image space, a mapping function may be determined that can be used to map any pixel in the inspection data (e.g., the live pixel stream) to its corresponding position in the die image space. In a similar manner, any pixel in the inspection data may be mapped to its corresponding position in the context space as described further below. Several other corrections may be used to provide substantially accurate mapping. For instance, corrections may be performed based on data provided by the inspection system such as pixel size in the x direction, which may be acquired by the run time alignment (RTA) subsystem of the inspection system, and stage calibration data. The mapping may be used for the die-to-die inspection mode. Mapping of the live pixel stream as described above may be performed in real-time during inspection of the wafer or subsequent to acquisition of the inspection data for the wafer. In this manner, determining the position of the inspection data in die image space may be performed during the inspection of the wafer. Alternatively, determining the position of the inspection data in the die image space may be performed subsequent to inspection of the wafer.

The methods described herein may or may not include acquiring the inspection data by performing inspection of a wafer. In other words, the methods described herein may be performed by a system (such as a system described further herein) that does not include an optical or electron beam inspection subsystem. Instead, the system may be configured as a "stand-alone" system that is configured to receive the inspection data from the inspection system. In this manner, the stand-alone system may acquire the inspection data from the inspection system. The stand-alone system may acquire the inspection data in any manner known in the art (e.g., via a transmission medium that may include "wired" and/or "wireless" portions). Alternatively, the method may be performed by a system that includes an inspection system. In this manner, the inspection system may form part of the system, and the inspection data may be acquired by the system by performing inspection of the wafer. In addition, regardless of the manner in which the inspection data is acquired, the methods described herein may be performed using any type of inspection data known in the art in any format known in the art. The inspection data may include data for a defect or defects detected on the wafer. The methods described herein may also be performed by a virtual inspector, examples of which are described in U.S. Pat. No. 8,126,255 to Bhaskar et al. issued on Feb. 28, 2012, which is incorporated by reference as if fully set forth herein. The embodiments described herein may be further configured as described in this patent.

In one embodiment, the position of the inspection data is determined with sub-pixel accuracy. For example, for substantially precise inspection of a wafer, the inspection pixel stream should be aligned to the high resolution stored die image to sub-pixel accuracy so that the micro care area (MCA) placement described further herein is substantially accurate. The embodiments described herein are advantageously capable of achieving this alignment accuracy during inspection.

In some embodiments, the method includes determining an offset between the data for the alignment sites on the wafer and the data for the predetermined alignment sites based on the aligning step, and determining the position of the inspection data is performed using the offset and the positions of the alignment sites in the die image space. For example, as each swath of the wafer is scanned, the alignment targets saved for the die-swath may be retrieved from the inspection recipe and the acquired wafer image can be searched for a match with the target images. The result of matching the target patch to the acquired image path is an alignment offset between the acquired image and the stored die image. That alignment offset can then be used to determine the position of other inspection data as described further herein.

In a further embodiment, the data for the alignment sites that is aligned includes data in each of multiple swaths of the inspection data acquired by the inspection system for the wafer, the alignment sites include at least one alignment site in each of the multiple swaths, determining the positions of the alignment sites includes determining the positions of the at least one alignment site in each of the multiple swaths in the die image space based on the predetermined positions of the predetermined alignment sites in the die image space, and determining the position of the inspection data includes determining the position of the inspection data in each of multiple swaths in the die image space based on the positions of the at least one alignment site in each of the multiple swaths in the die image space. For example, as described above, the alignment sites may be selected such that there is at least one alignment site in each swath of inspection data. Therefore, the alignment sites in each swath of inspection data can be individually aligned to the corresponding alignment sites. As such, the positions of the alignment sites in each swath of inspection data can be separately determined in die image space. Those determined positions can then be used as described further herein to align each swath of inspection data to the die image space.

In one embodiment, the method includes detecting defects on the wafer based on the inspection data, and locations of the defects are not known prior to the detecting of the defects. For example, the inspection methods described herein do not include revisiting defects that have been detected by another method or system. In other words, the embodiments described herein are not defect review methods or systems. Instead, the embodiments described herein are configured for examining locations on a wafer at which it is not known if defects are present or not.

In this manner, the embodiments described herein utilize a stored high resolution die image as a design data "proxy" for alignment purposes even though the inspection data produced by the methods and systems described herein and that is aligned is not necessarily produced at as high a resolution as the stored die image. For example, in defect review systems, the images generated by such systems are typically generated at such a high resolution (e.g., to determine sufficient defect information) that the patterns on the wafer appear substantially the same in images produced by such systems and in design data for the wafer (e.g., in the pre-OPC design data). Therefore, high resolution images of a least a portion of a die on the wafer can be easily acquired by the defect review system and aligned to a design or design data. As such, aligning defect review data to design data or its proxy is relatively straightforward. However, because inspection systems are typically not designed or used to produce images at the same or similar resolutions as defect review systems, aligning inspection system output to design is a much more difficult task. However, as described further herein, a stored high resolution die image can be used a proxy for design data for a wafer and the predetermined positions of predetermined alignment sites in that stored die image can be used to align inspection data to the die image and therefore the design proxy with substantially high accuracy.

Some embodiments described further herein include extracting different sensitivity regions for inspection using local image context determined from a previously stored high resolution image of a whole die. In other words, the method includes scanning the wafer, using the alignment site information to identify different sensitivity regions in the acquired image, and applying appropriate detection thresholds to the regions. These steps may be performed during an inspection scan. The methods rely on substantially accurate alignment of the inspection pixel grid to the alignment targets in the stored die image. This approach can be used in situations where the design data for the wafer is not readily available. In this manner, the embodiments described herein allow defining critical areas using a full die high resolution image as a "proxy" for design. In addition, the embodiments may include extracting MCAs from a stored high resolution full die image for use in a wafer inspection system.

In one embodiment, the method includes generating a context map from the stored high resolution die image, and the context map includes values for one or more attributes of the stored high resolution die image across the die image space. For example, the method may include analyzing the stored high resolution die image to generate a context map, which may include MCAs as described further herein in the stored die image. These step(s) may be performed during inspection recipe setup.

The stored high resolution die image may be analyzed frame by frame (a typical frame might be, for example, 8132 high resolution pixels by 8132 high resolution pixels, assuming that during inspection the frame size is 512 low resolution pixels by 512 low resolution pixels and the low resolution pixel is 16× the high resolution pixel). The analysis of the high resolution image frame results in the generation of a context map, which can be used in a number of ways described herein such as during inspection to inspect different regions of the die with different sensitivities based on the criticality of the regions. For example, areas where there are relatively thin dense lines or geometrical features relatively close to each other are more critical than areas where the geometries are wider in dimension and/or farther apart.

A set of user-defined rules can be used to categorize regions as critical or less critical. Given below are examples of rules one can use. The stored high resolution die images can be analyzed using any suitable morphological shape analysis algorithms to determine whether they satisfy a given rule.
1. Extract areas where lines (geometries) are closer than D nanometers.
2. Extract areas of relatively high curvature (such as corners and ends of lines).
3. Extract areas having relatively high curvature points that are closer than D nm from an adjacent feature (geometrical feature).
4. Extract lines that are thinner than D nanometers
5. Extract areas where lines are thinner than D nm and separated by less than D2 nm spacing.
6. Any Boolean function of the above features: for example, areas where there is a relatively high curvature (e.g., ends of lines) and relatively narrow spaces.
7. Spatial relationships between features can also be used, e.g., a relatively thin space (<D nm) between two opposite (oriented) relatively high curvature points.

Such regions of the frames can be extracted using standard image processing techniques such as binarization, or adaptive binarization, followed by binary morphological analysis to identify relatively thin lines and spaces and relatively small and large blobs, etc. Distances between these features can also be computed, and the rules can be applied to identify critical regions as described above. All frames of the high resolution die image may be analyzed in this manner to thereby generate inspection regions (also called MCAs) that will be used during inspection of that layer.

In one embodiment, the method includes determining a sensitivity for detecting defects on different portions of the wafer based on the position of the inspection data in the die image space, one or more attributes of the stored high resolution die image in the die image space, and one or more attributes of the inspection data, and the one or more attributes of the inspection data include one or more image noise attributes, if one or more defects were detected in the different portions, or some combination thereof. For example, care area information may be used to identify the different portions on the wafer and the sensitivity to be used to detect defects in the different portions. As such, the one or more attributes of the die image may include the care area information. However, the one or more attributes of the die image may also or alternatively include any of the attribute(s) of the die image described herein.

The data preparation phase may include creating or acquiring data for one or more attributes of the die image. The one or more attributes of the die image used to determine the sensitivity for detecting defects on different portions of the wafer may include process or yield information associated with die image. For example, in one embodiment, the one or more attributes of the die image are selected based on one or more attributes of previously acquired inspection data for the wafer, other wafers, or some combination thereof for the die image, different die images, or some combination thereof for a process layer for which the inspection data for the wafer was acquired, for different process layers, or some combination thereof. In this manner, the one or more attributes of the die image in the die image space used to determine the sensitivity for detecting defects on different portions of the wafer may be selected based on a correlation to attributes of previously collected inspection data from the same wafer or different wafers on the same or different designs on the same or different process layers. The previously collected inspection data may be stored in a data structure such as a fab database or any other suitable database, file, etc. or may be included in a knowledge base. In this manner, the one or more attributes of the die image may be selected in this embodiment based on cumulative learning, historical data, or a training set of data.

The one or more attributes of the inspection data used in this embodiment may include image noise attributes and/or the detection or non-detection of defects in different regions of the inspection data. The attribute(s) of the inspection data used in this step may include any other attributes of the inspection data described herein. Determining the sensitivity in this embodiment may be performed for region based multi-threshold (RBMT) setup for the inspection process based on image noise correlated to design attributes. Determining the sensitivity in this embodiment may be further performed as described herein.

In one such embodiment, the one or more attributes of the stored high resolution die image are selected based on yield criticality of defects previously detected in the different portions, fault probability of the defects previously detected in the different portions, or some combination thereof. In this manner, the sensitivity for detecting the defects may be based at least in part on one or more attributes of the die image that are selected based on the yield criticality and/or fault probability of defects detected in the different portions. The process or yield criticality information may include, for example, critical defects determined by process window qualification (PWQ), locations of defects of interest (DOI) based on hot spots (e.g., determined from inspection), hot spot information determined from logical bitmaps, a kill probability (KP) value determined from test results for a defect detected at a hot spot, any other process or yield information, or some combination thereof. A "hot spot" may be generally defined as a location in the design printed on the wafer at which a killer defect may be present. In contrast, a "cold spot" may be generally defined as a location in the design printed on the wafer at which a nuisance defect may be present.

Data for the one or more attributes of the die image may also be referred to as "context" data that defines geometrical areas in the die image that have different values of one or more attributes (e.g., type(s) of features within the areas such as contact areas or dummy fill areas, "where to inspect" information or "care areas," "critical" areas in which a process failure is possible, or some combination thereof). The term context data is used interchangeably herein with the terms "context information" and "context map." The context information may be acquired from a variety of sources including simulation, modeling, and/or analysis software products that are commercially available from KLA-Tencor, other software such as design rule checking (DRC) software, or some combination thereof. Furthermore, additional context data may be determined and combined with data for the attribute(s) of the die image. A data structure such as a database or file including the die image and/or the context data may have any suitable format known in the art.

In an additional embodiment, the method includes determining a sensitivity for detecting defects on different portions of the wafer based on the position of the inspection data in the die image space and a context map, and the context map includes values for one or more attributes of the stored high resolution die image across the die image space. For example, the method may include using the context map to define relatively high sensitivity regions in a die on the wafer for critical regions and variable sensitivity regions based on criticality of context. In one example, segments of the die image may be defined to isolate dense arrays and logic, open areas, and grainy metal. A combination of image gray level and context may also be used to define one or more segments in the die image. For example, pixels having an intermediate gray level may be combined in one segment. The image gray levels may be determined using an image acquired by the inspection system or other image acquisition system.

In some embodiments, determining the sensitivity for detecting the defects on different portions of the wafer based on the position of the inspection data in the die image space and a context map is performed by the inspection system during inspection of the wafer. For example, the context map may be used by the inspection system as described herein when inspecting a wafer. In another embodiment, determining the sensitivity for detecting the defects on different portions of the wafer based on the position of the inspection data in the die image space and a context map is performed by the inspection system after acquisition of the inspection data for the wafer has been completed. For example, the context map may be used by the inspection system as described above after the inspection data is available offline.

In another embodiment, the method includes identifying one or more care areas to be used for inspection of the wafer based on the stored high resolution die image. For example, the method may use the context map to automatically define dummy areas (do not inspect regions) of the die on the wafer and to define coarse regions of the die for which different sensitivity thresholds are to be used. In one such example, the context map (e.g., a context map that defines dummy fill areas) may be used to automatically define do not care regions which require no inspection and can therefore be excluded for purposes of defect detection. Such regions are typically less well controlled and therefore produce a relatively large amount of noise (when comparing die-to-die). Therefore, excluding such regions may increase the overall S/N of inspection.

In one embodiment, determining the sensitivity for detecting defects on different portions of the wafer based on the position of the inspection data in die image space and a context map includes determining sensitivity thresholds used with the inspection data to detect the defects on the different portions of the wafer. In this manner, the sensitivity may be altered from region-to-region by altering one or more thresholds used for defect detection, which is analogous to segmented automatic threshold (SAT) methods. For example, low threshold (high sensitivity) detection can be used for critical regions, and high threshold (low sensitivity) detection can be used for non-critical regions. By segmenting the inspection data and varying the threshold(s) used for defect detection based on one or more attributes of the die image, the overall sensitivity of the inspection process can be increased. Therefore, the methods and systems described herein provide improved defect detection.

In some embodiments, the method includes identifying the inspection data that corresponds to a care area on the wafer based on the position of the inspection data in the die image space. For example, a MCA map may be defined using the stored die image coordinates. Then, an offset to be applied to this map may be determined in order to substantially accurately know which sensitivity region each pixel (or one or more pixels) in the acquired swath fall into. The detection algorithm can then apply the appropriate threshold pertinent to that sensitivity region.

In an additional embodiment, the method includes acquiring information for a hot spot at one location on the wafer, identifying other locations of the hot spot on the wafer based on the information for the hot spot, and generating care areas for the wafer based on the hot spots at the one location and the other locations. For example, so-called "hot spots" that are known (e.g., through simulations or prior knowledge) areas of weaknesses in the layout may be used to identify critical areas. If there are examples in the stored die image of each hot spot (or one or more hot spots), simple normalized cross-correlation can be used to identify all other locations in the die where such geometry is present. All frames of the high resolution die image may be analyzed in this manner to thereby generate inspection regions (also called MCAs) that will be used during inspection of that layer.

The embodiments described herein may include detecting defects on the wafer based on the inspection data. The defect detection may be performed at any point during or after acquisition of the inspection data. Detecting the defects on the wafer may be performed based on the location of the inspection data in die image space and one or more defect detection parameters determined as described herein (e.g., sensitivity, care areas, etc.). However, the inspection data may be used as input to any suitable defect detection algorithm and/or method known in the art. In other words, the inspection data described herein is not specific to any one or more defect detection methods and/or algorithms. Results of the defect detection may include die image space positions of the defects as well as any other information that can be determined by the method and/or system based on the inspection data corresponding to the defects.

Some embodiments described further herein include classifying defects using local image context determined from a previously stored high resolution image of a whole die. The methods rely on substantially accurate alignment of the inspection pixel grid to the alignment targets in the stored die image. This approach can be used in situations where the design data for the wafer is not readily available.

In one embodiment, the method includes detecting defects on the wafer based on the inspection data, which may be performed as described herein, and classifying at least one of the defects based on the position of the inspection data corresponding to the at least one defect in the die image space and a context map, and the context map includes values for one or more attributes of the stored high resolution die image across the die image space. In this manner, the method may include classifying defects according to their locations in the context map. The context map may be determined as described herein and since the context map will be determined in die image space and the location of the inspection data (and thus the inspection data corresponding to defects) is determined in die image space, the values of the context map at the location of the defect can be easily determined. Those values in the context map may then be used to classify the defect in a number of different ways (e.g., based on the criticality of the region in which the defect is located, based on the yield relevance of the defect, etc.). This step may be performed during an inspection scan.

In an additional embodiment, the method includes generating a context map from the stored high resolution die image, the context map includes values for one or more attributes of the stored high resolution die image across the die image space and context codes for the values, and the method includes detecting defects on the wafer based on the inspection data and assigning one of the context codes to at least one of the defects based on the position of the inspection data corresponding to the at least one defect in the die image space and the context map. The context map may be generated according to any of the embodiments described herein. In addition, each region of the stored die image may be tagged with a certain context code (bin code). In this manner, once a defect is found, its context can be computed using a lookup table where the table maps each small region of the stored die image to some specific context code.

In another embodiment, the inspection data includes data for defects on the wafer, and the method includes determining positions of the defects in the die image space based on the position of the inspection data in the die image space, determining if the defects are nuisance defects based on the positions of the defects in the die image space and one or more attributes of the stored high resolution die image in the die image space, and determining if the defects not determined to be nuisance defects are systematic or random defects based on the one or more attributes of the stored high resolution die image in the die image space. A "nuisance" or "nuisance defect" is a term commonly used in the art to refer to a potential defect that is detected on a wafer, but that is not an actual defect that is of interest to a user. In this manner, a "nuisance defect" may simply be noise on the wafer that is detected by inspection, which is not representative of any actual defect on the wafer, or an actual defect that the user does not care about.

The one or more attributes of the die image used to identify nuisance defects in this step may include any of the attribute(s) described herein. For example, the one or more attributes of the die image may be defined in the context map. In this manner, the method may include applying the context map to defect data to filter (e.g., discard) defects considered not important (e.g., nuisance defects) in applications such as, but not limited to, PWQ. As such, portions of the design that are approaching the limits of the capabilities of the fabrication processes may be separated into portions that are critical and portions that are not critical based on the context. In another example, the attribute(s) of the die image used to identify nuisance defects in this step include hot spot information for the die image. In this manner, the positions of the defects in die image space and the hot spot information may be used to identify defects not detected at hot spots and/or detected at cold spots in the die image as nuisance defects.

PWQ applications for lithography generally involve exposing dies on a wafer at different exposure dosages and focus offsets (i.e., at modulated dose and focus) and identifying systematic defects in the dies that can be used to determine areas of design weakness and to determine the process window. Examples of PWQ applications for lithography are illustrated in commonly assigned U.S. Pat. No. 7,729,529 to Wu et al. issued on Jun. 1, 2010, which is incorporated by reference as if fully set forth herein. Many artifacts of focus and exposure modulation can appear as defects (die-to-standard reference die differences), but are in fact nuisance defects. Examples of such artifacts may include CD variations and line-end pullbacks or shortening in regions in which these artifacts have no or little impact on yield or performance of the device. However, the position of a defect may be determined substantially accurately with respect to the die image space using the methods described herein. In addition, the methods described herein can be used to determine care areas with relatively high accuracy as described further above. These "micro" care areas can be centered on known hot spots and inspected with relatively high sensitivity or may be centered on known cold-spots (systematic nuisance) as don't care areas or areas inspected with relatively low sensitivity.

Determining if the defects not determined to be nuisance defects are systematic or random defects may be performed based on one or more attributes of the die image in the die image space (which may be defined in the context map as described further above) or by comparing the positions of the defects to positions of hot spots, which may be stored in a data structure such as a list or database. In addition, all of the defects not of interest may not be nuisance defects. For instance, systematic defects that have relatively low or no yield impact may be defects not of interest and not nuisance defects. Such defects may appear on the active pattern or device area on the wafer. The methods described herein may include identifying such defects. Such defects, or defects located at cold spots, may be identified from the design context (e.g., redundant vias), modeling, PWQ, inspection and review, and defect correlation with test (e.g., relatively high stacked defect density at a location with relatively low stacked electrical fault locations, etc.). In addition, monitoring of these defects may be performed by comparing the positions of the defects with the positions of hot spots and cold spots. Furthermore, discovery of the systematic defects may be performed by correlating multiple sources of input from design, modeled results, inspection results, metrology results, and test and failure analysis (FA) results.

Systematic DOI may include all pattern dependent defect types. Identifying systematic defects is advantageous such that the impact that these defects will have on devices can be analyzed. Random DOI may include a statistical sample of critical types of random defects. Identifying random defects is advantageous since critical types of random defects can be analyzed to determine the impact that these defects will have on devices. In addition, by identifying the random defects, one or more inspection process parameters may be altered to suppress the detection of random defects that can be considered nuisance defects. Furthermore, the inspection process parameter(s) may be altered to distinguish nuisance defects from systematic causes (cold spots).

Determining if defects are nuisance, systematic, or random defects is also advantageous since yield can be predicted more accurately based on the types of defects that are detected on a wafer or wafers and the relevance to the yield that the different types of defects have. In addition, the results of the methods described herein, possibly in combination with the yield predictions, may be used to make one or more decisions regarding the design data and the manufacturing process. For example, the results of the methods described herein may be used to alter one or more parameters of a process or processes used to fabricate the wafer level being inspected. Preferably, the one or more parameters of the process(es) are altered such that fewer systematic defects and/or fewer types of systematic defects, and possibly fewer critical random defects and/or fewer types of critical random defects, are caused by the process(es).

In some embodiments, the wafer and additional wafers are processed using wafer level process parameter modulation, and the method includes detecting defects on the wafer and the additional wafers by comparing inspection data for die on the wafer and the additional wafers to a common standard reference die. In this manner, defect detection may be performed in wafer-to-wafer inspection mode. In one such embodiment, data for alignment sites on one wafer may be aligned to data for the predetermined alignment sites, and the data for the alignment sites on this wafer may be aligned to data for the alignment sites on another wafer. Alternatively, data for alignment sites on both wafers may be aligned to data for the predetermined alignment sites including any of the data described herein. In this manner, after data for the alignment sites on the wafers have been aligned to the data for the predetermined alignment sites, the inspection data for the wafers will effectively be aligned to each other and can be overlaid or compared for defect detection.

In some embodiments, the wafer-to-wafer inspection mode involves using a reference die that that exists outside of the wafer being inspected (i.e., an off-wafer reference). Implementation of this method is far from straightforward since it involves separating the runtime feedback concepts that are currently used to enable inspection systems to accomplish die-to-die level overlay tolerances (e.g., 0.1 pixel) to achieve adequate sensitivity results.

The methods described herein can, therefore, be used to enable comparison of wafers to one another, which is a potentially extremely useful application. One motivation for defect inspection using wafer-to-wafer comparison is to discover "systematic defect mechanisms" that may result from the interaction of a specific circuit layout and the stacked tolerances of the wafer manufacturing process. This discovery process may include comparing wafers on which the same device design was printed but which were processed differently. The most deterministic approach is to modulate process parameters in a single- or multi-variable experiment (e.g., using a methodical design of experiments (DOE) approach). In one embodiment, the wafer and additional wafers (e.g., two or more wafers) are processed using wafer level process parameter modulation, which may be performed as described above or in any other suitable manner. The process parameters may be modulated to cause the measurable physical and/or electrical attributes of the resulting wafers to approach their allowable limits. In addition, the method may include detecting defects on the wafer and the additional wafers by comparing inspection data for die on the wafer and the additional wafers to a common standard reference die. Detecting the defects on the wafers in this manner may be performed as described further herein. In one such embodiment, the method may include determining if structural differences between wafers occur as measured by the detection of "defects." Such an approach may be referred to as integrated PWQ (iPWQ). In this manner, the methods described herein may be used to enable the implementation of iPWQ (e.g., using the standard reference die approach for iPWQ). As such. PWQ methodology may be extended to include wafer level process parameter modulation and comparison of die on different wafers to a common standard reference die for purposes of implementing the iPWQ methodology.

In contrast, discovery of lithography induced "systematic defect mechanisms" may be performed using methods described in U.S. Pat. No. 6,902,855 to Peterson et al., which is incorporated by reference as if fully set forth herein, and the PWQ product commercially available from KLA-Tencor. PWQ leverages the unique ability of lithography tools to modulate lithography exposure process parameters at the reticle shot level using focus and exposure as variables to determine design-lithography interactions. This application is often used for OPC verification. However, PWQ is limited to the direct comparison of dies on a wafer that are printed with modulated focus and/or exposure parameters. The impact of other process variables associated with process steps such as etch, deposition, thermal processing, chemical-mechanical polishing (CMP), etc. cannot be directly assessed by PWQ since these variables can only be modulated at the wafer level. However, systematic defect mechanisms associated with or caused by these process variables can be discovered using the methods described herein. In particular, the methods described herein can be used to examine non-lithography process modulation in a PWQ-type application by wafer-to-wafer comparison.

In one embodiment, the method is performed during inspection of the wafer. For example, the method may be performed while or during scanning of a wafer by the inspection system (i.e., as the inspection data is being generated). In particular, aligning the data for the alignment sites with data for the predetermined alignment sites, determining the positions of the alignment sites in the die image space, and determining the position of the inspection data in the die image space may be performed during inspection of the wafer (i.e., during run time). Steps of the method that are performed to setup these steps (e.g., alignment site selection) may be performed prior to inspection of the wafer. In addition, all or some of the steps of the method may be performed after all of the inspection data has been generated for the wafer.

In an additional embodiment, setup of the method is performed on-tool. In other words, setup of the method may be performed on the inspection system that will be used to generate the inspection data that will be aligned in the method. Such embodiments may be useful when the inspection system can generate a die image having sufficiently high resolution as described herein. Alternatively, a high resolution die image may be generated by a system other than the inspection system and then the method may be setup (e.g., selection of the predetermined alignment sites, etc.) using the inspection system, including the optical elements of the inspection system as well as the computer subsystem(s) of the inspection system.

In another embodiment, setup of the method is performed off-tool. In other words, setup of the method may be performed on a system other than the inspection system that will be used to generate the inspection data that will be aligned in the method. The system that performs setup of the method off-tool may include, for example, a microscope (optical or electron beam), a review system, a system into which the wafer is not or cannot be loaded (e.g., a stand-alone computer system), or any other appropriate system known in the art that can be configured to perform setup of the method. For example, setup of the method may be performed with an electron beam-based imaging system that generates the high resolution die image and one or more computer systems that select the predetermined alignment sites and generate any other information that is needed to perform the steps of the method described herein.

Aligning the data, determining the positions of the alignment sites, and determining the position of the inspection data are performed by a computer system, which may be configured according to any of the embodiments described herein.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a non-transitory computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method detects the defects, the method may include storing information about the detected defects in a storage medium.

An additional embodiment relates to a non-transitory computer-readable medium storing program instructions executable on a computer system for performing a computer-implemented method for determining a position of inspection data with respect to a stored high resolution die image. One such embodiment is shown in FIG. 1. In particular, as shown in FIG. 1, non-transitory computer-readable medium 100 includes program instructions 102 executable on computer system 104. The computer-implemented method includes the steps of the method described above. The computer-implemented method for which the program instructions are executable may include any other step(s) described herein.

Program instructions 102 implementing methods such as those described herein may be stored on computer-readable medium 100. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 2:
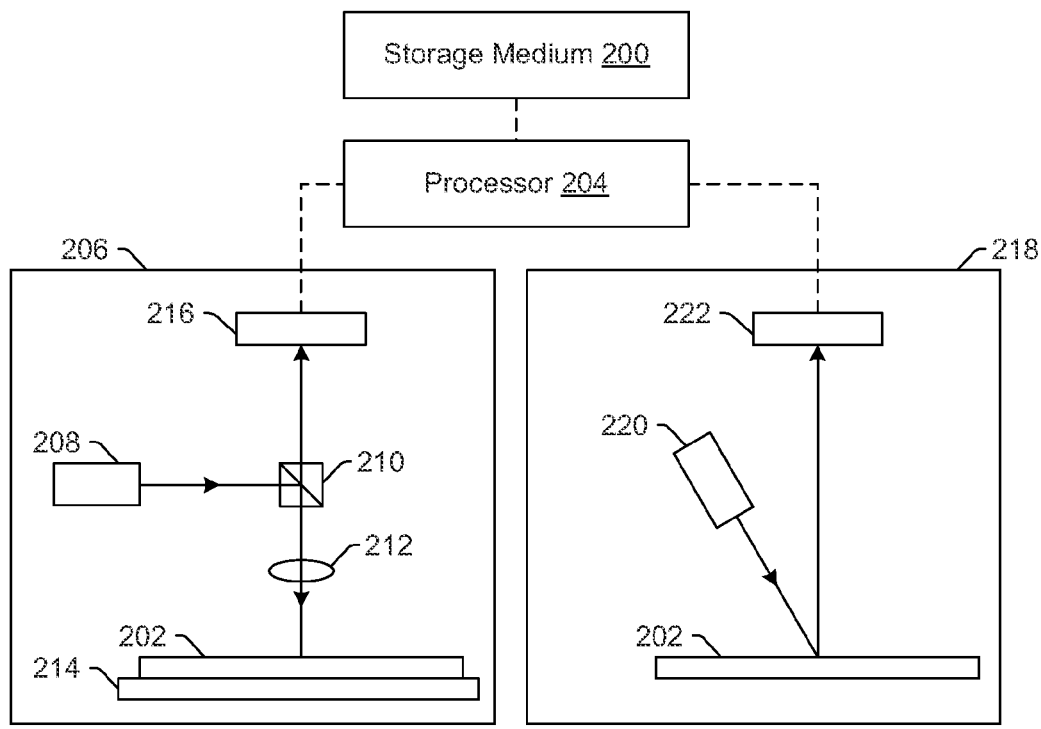
FIG. 2 is a schematic diagram illustrating a side view of one embodiment of a system configured to determine a position of inspection data with respect to a stored high resolution die image.

Another embodiment relates to a system configured to determine a position of inspection data with respect to a stored high resolution die image. One embodiment of such a system is shown in FIG. 2. The system includes storage medium 200 that includes a stored high resolution die image for wafer 202. The storage medium may include any of the storage media described herein. The stored high resolution die image may include any of the high resolution die images described herein and may be stored as described further herein.

The system also includes processor 204 coupled to storage medium 200. The processor may be coupled to the storage medium in any suitable manner (e.g., by one or more transmission media shown in FIG. 2 by the dashed lines, which may include "wired" and/or "wireless" transmission media) such that the processor may receive information and images stored in the storage medium and possibly store and/or alter information and/or images in the storage medium. The processor may be a processor included in a computer system, and the computer system including such a processor may be further configured as described herein.

The processor is configured for performing the aligning data for alignment sites, determining positions of the alignment sites, and determining the position of the inspection data steps described further herein. The processor may be configured to perform these steps according to any of the embodiments described herein and may be configured to perform any other step(s) of any embodiment(s) described herein.

Another embodiment of a system configured to determine a position of inspection data with respect to a stored high resolution die image includes the storage medium and the processor configured as described above as well as an inspection system configured to acquire data for alignment sites on a wafer and inspection data for the wafer. For example, as shown in FIG. 2, one embodiment of the system includes inspection system 206. The inspection system may be a relatively high speed, low resolution tool compared to the system that acquires the high resolution die image for the wafer. In one such example, the inspection system may be a light-based, or optical, wafer inspection system, including any of those commercially available from suppliers such as KLA-Tencor.

As shown in FIG. 2, the inspection system includes light source 208. Light source 208 may include any suitable light source known in the art such as a laser. Light source 208 is configured to direct light to beam splitter 210, which is configured to reflect the light from light source 208 to refractive optical element 212. Refractive optical element 212 is configured to focus light from beam splitter 210 to wafer 202. Beam splitter 210 may include any suitable beam splitter such as a 50/50 beam splitter. Refractive optical element 212 may include any suitable refractive optical element, and although refractive optical element 212 is shown in FIG. 2 as a single refractive optical element, it may be replaced with one or more refractive optical elements and/or one or more reflective optical elements.

Light source 208, beam splitter 210, and refractive optical element 212 may, therefore, form an illumination channel for the inspection system. The illumination channel may include any other suitable elements (not shown in FIG. 2) such as one or more polarizing components and one or more filters such as spectral filters. As shown in FIG. 2, the light source, beam splitter, and refractive optical element are configured such that the light is directed to the wafer at a normal or substantially normal angle of incidence. However, the light may be directed to the wafer at any other suitable angle of incidence (e.g., an oblique angle of incidence).

The inspection system may be configured to scan the light over the wafer in any suitable manner. For example, the wafer may be positioned on stage 214 that is part of a mechanical and/or robotic assembly (not shown), which is configured to move the wafer with respect to the optical elements of the inspection system such that light from the inspection system can be scanned over the wafer while light from the wafer is detected.

Light reflected from wafer 202 due to illumination may be collected by refractive optical element 212 and directed through beam splitter 210 to detector 216. Therefore, the refractive optical element, beam splitter, and detector may form a detection channel of the inspection system. The detector may include any suitable imaging detector known in the art such as a charge coupled device (CCD). This detection channel may also include one or more additional components (not shown in FIG. 2) such as one or more polarizing components, one or more spatial filters, one or more spectral filters, and the like. Detector 216 is configured to generate inspection data that may include any of the data described further herein.

As described above, the detector included in the inspection system may be configured to detect light reflected from the wafer. Therefore, the detection channel included in the inspection system may be configured as a BF channel. However, the inspection system may include one or more detection channels (not shown) that may be used to detect light scattered from the wafer due to illumination of the wafer. In addition, one or more parameters of the detection channel shown in FIG. 2 may be altered such that the detection channel detects light scattered from the wafer. In this manner, the inspection system may be configured as a DF tool and/or a BF tool.

In one embodiment, the system includes an electron beam-based imaging system configured for acquiring the high resolution die image for the wafer by scanning a die on the wafer or another wafer and storing the acquired high resolution die image in the storage medium. For example, as shown in FIG. 2, the system may include electron beam-based imaging system 218 configured for acquiring the high resolution die image for the wafer by scanning a die on wafer 202. Imaging system 218 may be configured as an EBR tool, including any electron beam defect review tool commercially available from suppliers such as KLA-Tencor. Imaging system 218 may also or alternatively be configured as an electron beam-based metrology tool such as a SEM or any other electron beam-based metrology tool commercially available from suppliers such as KLA-Tencor.

The electron beam-based imaging system may be capable of a higher resolution than the inspection system, but may not be capable of as high a speed as the inspection system. In other words, the inspection system is capable of a higher scanning speed than the electron beam-based imaging system. In one such example, the inspection system may be configured to scan light over a relatively large portion of the wafer while acquiring output (e.g., images or image data), but the electron beam-based imaging system may be configured to scan only a substantially small portion of the wafer while acquiring output.

The electron beam-based imaging system is shown in FIG. 2 as having a generic configuration for a SEM. In particular, as shown in FIG. 2, the electron beam-based imaging system may include electron beam source 220 that is configured to generate a beam of electrons that are directed to wafer 202 at a suitable angle of incidence by one or more focusing and/or directing elements (not shown). Electrons that are returned from the wafer due to the electron beam incident thereon may be detected by detector 222. The electrons that are returned from the wafer may be directed and focused on the detector using any suitable focusing and/or directing elements (not shown). Detector 222 may include any suitable imaging detector that can generate a high resolution die image described herein in response to the electrons returned from the wafer.

The processor of the system is coupled to the inspection system and may also be coupled to the electron beam-based imaging system. For example, the processor may be coupled to detectors of the inspection system and possibly the electron beam-based imaging system. In one such example, as shown in FIG. 2, processor 204 is coupled to detector 216 of inspection system 206 and detector 222 of imaging system 218 (e.g., by one or more transmission media shown by the dashed lines in FIG. 2, which may include any suitable transmission media known in the art). The processor may be coupled to the detectors in any suitable manner. In another example, the processor may be coupled to individual computer systems (not shown) of the inspection system and the imaging system. The processor may be coupled to the inspection system and the imaging system in any other suitable manner such that image(s) and any other information for the wafer generated by the inspection system and the imaging system can be sent to the processor and, optionally, such that the processor can send instructions to the inspection system and the imaging system to perform one or more steps described herein (e.g., acquiring the inspection data with the inspection system and/or acquiring the high resolution die image with the electron beam-based imaging system).

The processor is configured for performing the aligning data for alignment sites, determining positions of the alignment sites, and determining the position of the inspection data steps described further herein. The processor may be configured to perform these steps according to any of the embodiments described herein and may be configured to perform any other step(s) of any embodiment(s) described herein. The system shown in FIG. 2 may be further configured as described herein.

It is noted that FIG. 2 is provided herein to generally illustrate one configuration of the inspection system and electron beam-based imaging system that may be included in the system embodiments described herein. Obviously, the configuration of the inspection system and electron beam-based imaging system described herein may be altered to optimize the performance of the system as is normally performed when designing a commercial inspection or electron beam-based imaging system. In addition, the systems described herein may be implemented using an existing inspection system (e.g., by adding functionality described herein to an existing inspection system) such as the 28XX, 29XX, and Puma 9XXX series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for determining a position of inspection data with respect to a stored high resolution die image are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for determining a position of inspection data with respect to a stored high resolution die image, comprising:
    aligning data acquired by an inspection system for alignment sites on a wafer with data for predetermined alignment sites, wherein the predetermined alignment sites have predetermined positions in die image space of a stored high resolution die image for the wafer;
    determining positions of the alignment sites in the die image space based on the predetermined positions of the predetermined alignment sites in the die image space; and
    determining a position of inspection data acquired for the wafer by the inspection system in the die image space based on the positions of the alignment sites in the die image space, wherein aligning the data, determining the positions of the alignment sites, and determining the position of the inspection data are performed by a computer system.

2. The method of claim 1, wherein the stored high resolution die image is a stored high resolution image of an entirety of the die.

3. The method of claim 1, further comprising acquiring the high resolution die image for the wafer by scanning a die on the wafer or another wafer with an electron beam-based imaging system and storing the acquired high resolution die image in a storage medium.

4. The method of claim 1, wherein design data for the wafer is not available for use in the method.

5. The method of claim 1, further comprising detecting defects on the wafer based on the inspection data, wherein locations of the defects are not known prior to said detecting.

6. The method of claim 1, wherein the position of the inspection data is determined with sub-pixel accuracy.

7. The method of claim 1, further comprising identifying one or more care areas to be used for inspection of the wafer based on the stored high resolution die image.

8. The method of claim 1, further comprising identifying the inspection data that corresponds to a care area on the wafer based on the position of the inspection data in the die image space.

9. The method of claim 1, further comprising determining an offset between the data for the alignment sites on the wafer and the data for the predetermined alignment sites based on said aligning, wherein determining the position of the inspection data is performed using the offset and the positions of the alignment sites in the die image space.

10. The method of claim 1, further comprising generating a context map from the stored high resolution die image, wherein the context map comprises values for one or more attributes of the stored high resolution die image across the die image space.

11. The method of claim 1, further comprising acquiring information for a hot spot at one location on the wafer, identifying other locations of the hot spot on the wafer based on the information for the hot spot, and generating care areas for the wafer based on the hot spots at the one location and the other locations.

12. The method of claim 1, further comprising detecting defects on the wafer based on the inspection data and classifying at least one of the defects based on the position of the inspection data corresponding to the at least one defect in the die image space and a context map, wherein the context map comprises values for one or more attributes of the stored high resolution die image across the die image space.

13. The method of claim 1, further comprising generating a context map from the stored high resolution die image, wherein the context map comprises values for one or more attributes of the stored high resolution die image across the die image space and context codes for the values, detecting defects on the wafer based on the inspection data, and assigning one of the context codes to at least one of the defects based on the position of the inspection data corresponding to the least one defect in the die image space and the context map.

14. The method of claim 1, further comprising selecting the predetermined alignment sites based on information about one or more optical modes and pixel size to be used by the inspection system for inspection of the wafer.

15. The method of claim 1, wherein the data acquired for the alignment sites on the wafer and the inspection data are acquired with two or more optical modes on the inspection system.

16. The method of claim 15, wherein the alignment sites used for a first of the two or more optical modes are different from the alignment sites used for a second of the two or more optical modes.

17. The method of claim 15, wherein the data for the predetermined alignment sites used for a first of the two or more optical modes is different than the data for the predetermined alignment sites used for a second of the two or more optical modes.

18. The method of claim 1, wherein the method is performed during inspection of the wafer.

19. The method of claim 1, wherein the data for the alignment sites on the wafer comprises scanned images, and wherein the data for the predetermined alignment sites comprises high resolution image data from the stored high resolution die image.

20. The method of claim 1, wherein the data for the alignment sites on the wafer comprises scanned images, and wherein the data for the predetermined alignment sites comprises image clips.

21. The method of claim 1, further comprising selecting the predetermined alignment sites from the stored high resolution die image for the wafer such that there is at least one predetermined alignment site in each of multiple swaths of the inspection data.

22. The method of claim 1, wherein said aligning is performed before defect detection for the wafer.

23. The method of claim 1, wherein setup of the method is performed off-tool.

24. The method of claim 1, wherein setup of the method is performed on-tool.

25. The method of claim 1, further comprising selecting the predetermined alignment sites by dividing the stored high resolution die image into portions that correspond to each of multiple swaths of the inspection data and searching the stored high resolution die image to identify and select at least one of the predetermined alignment sites in each of the multiple swaths.

26. The method of claim 1, further comprising extracting high resolution die image clips for the predetermined alignment sites from the stored high resolution die image and storing the extracted image clips in a file that is used by the inspection system for inspection of the wafer.

27. The method of claim 1, further comprising selecting the predetermined alignment sites by pre-processing the stored high resolution die image to select predetermined alignment sites that are compatible with the inspection system and an inspection process to be used by the inspection system for the wafer.

28. The method of claim 1, further comprising selecting the predetermined alignment sites by scanning a die row on a wafer using the inspection system and processing each frame of a die to identify unique alignment sites.

29. The method of claim 1, further comprising scanning the wafer using the best imaging mode of the inspection system for inspection to select suitable predetermined alignment sites and determining positions of the selected predetermined alignment sites based on images produced by said scanning and the stored high resolution die image.

30. The method of claim 1, wherein the alignment sites comprise more than one alignment site in each of multiple swaths of the inspection data.

31. The method of claim 1, wherein the alignment sites comprise more than one alignment site in each of multiple swaths of the inspection data to correct scaling errors.

32. The method of claim 1, wherein the predetermined alignment sites are selected at a predetermined frequency across a die on the wafer.

33. The method of claim 1, wherein the predetermined alignment sites are distributed over a die on the wafer at a predetermined minimum interval distance.

34. The method of claim 1, further comprising aligning the inspection system to the alignment sites to correct stage positional accuracy, rotational errors, x and y translational errors, scaling errors, or some combination thereof in the inspection system.

35. The method of claim 1, further comprising selecting the predetermined alignment sites to include a set of alignment features that in combination provide sufficient alignment information for said determining the positions of the alignment sites.

36. The method of claim 1, wherein the inspection system is configured to use a bright field mode for inspection of the wafer.

37. The method of claim 1, wherein the inspection system is configured to use a dark field mode for inspection of the wafer.

38. The method of claim 1, wherein the inspection system is configured to use an electron beam imaging mode for inspection of the wafer.

39. The method of claim 1, further comprising determining a sensitivity for detecting defects on different portions of the wafer based on the position of the inspection data in the die image space, one or more attributes of the stored high resolution die image in the die image space, and one or more attributes of the inspection data, wherein the one or more attributes of the inspection data comprise one or more image noise attributes, if one or more defects were detected in the different portions, or some combination thereof.

40. The method of claim 39, wherein the one or more attributes of the stored high resolution die image are selected based on yield criticality of defects previously detected in the different portions, fault probability of the defects previously detected in the different portions, or some combination thereof.

41. The method of claim 1, further comprising determining a sensitivity for detecting defects on different portions of the wafer based on the position of the inspection data in the die image space and a context map, wherein the context map comprises values for one or more attributes of the stored high resolution die image across the die image space.

42. The method of claim 1, wherein the inspection data comprises data for defects on the wafer, the method further comprising determining positions of the defects in the die image space based on the position of the inspection data in the die image space, determining if the defects are nuisance defects based on the positions of the defects in the die image space and one or more attributes of the stored high resolution die image in the die image space, and determining if the defects not determined to be nuisance defects are systematic or random defects based on the one or more attributes of the stored high resolution die image in the die image space.

43. The method of claim 1, wherein the wafer and additional wafers are processed using wafer level process parameter modulation, and wherein the method further comprises detecting defects on the wafer and the additional wafers by comparing inspection data for die on the wafer and the additional wafers to a common standard reference die.

44. The method of claim 1, wherein the data for the alignment sites that is aligned comprises data in each of multiple swaths of the inspection data acquired by the inspection system for the wafer, wherein the alignment sites comprise at least one alignment site in each of the multiple swaths, wherein determining the positions of the alignment sites comprises determining the positions of the at least one alignment site in each of the multiple swaths in the die image space based on the predetermined positions of the predetermined alignment sites in the die image space, and wherein determining the position of the inspection data comprises determining the position of the inspection data in each of the multiple swaths in the die image space based on the positions of the at least one alignment site in each of the multiple swaths in the die image space.

45. A system configured to determine a position of inspection data with respect to a stored high resolution die image, comprising:
- a storage medium comprising a stored high resolution die image for a wafer, and
- a processor coupled to the storage medium, wherein the processor is configured for:
  - aligning data acquired by an inspection system for alignment sites on the wafer with data for predetermined alignment sites, wherein the predetermined alignment sites have predetermined positions in die image space of the stored high resolution die image for the wafer,
  - determining positions of the alignment sites in the die image space based on the predetermined positions of the predetermined alignment sites in the die image space; and
  - determining a position of inspection data acquired for the wafer by the inspection system in the die image space based on the positions of the alignment sites in the die image space.

46. A system configured to determine a position of inspection data with respect to a stored high resolution die image, comprising:
- an inspection system configured to acquire data for alignment sites on a wafer and inspection data for the wafer;
- a storage medium comprising a stored high resolution die image for the wafer; and
- a processor coupled to the inspection system and the storage medium, wherein the processor is configured for:
  - aligning the data acquired by the inspection system for the alignment sites on the wafer with data for predetermined alignment sites, wherein the predetermined alignment sites have predetermined positions in die image space of the stored high resolution die image for the wafer;
  - determining positions of the alignment sites in the die image space based on the predetermined positions of the predetermined alignment sites in the die image space; and
  - determining a position of the inspection data acquired for the wafer by the inspection system in the die image space based on the positions of the alignment sites in the die image space.

47. The system of claim 46, wherein the stored high resolution die image is a stored high resolution image of an entirety of the die.

48. The system of claim 46, further comprising an electron beam-based imaging system configured for acquiring the high resolution die image for the wafer by scanning a die on the wafer or another wafer and storing the acquired high resolution die image in the storage medium.

49. The system of claim 46, wherein design data for the wafer is not available for use by the system.

50. The system of claim 46, wherein the processor is further configured for detecting defects on the wafer based on the inspection data, and wherein locations of the defects are not known prior to said detecting.

51. The system of claim 46, wherein the position of the inspection data is determined with sub-pixel accuracy.

52. The system of claim 46, wherein the processor is further configured for identifying one or more care areas to be used for inspection of the wafer based on the stored high resolution die image.

53. The system of claim 46, wherein the processor is further configured for identifying the inspection data that corresponds to a care area on the wafer based on the position of the inspection data in the die image space.

54. The system of claim 46, wherein the processor is further configured for determining an offset between the data for the alignment sites on the wafer and the data for the predetermined alignment sites based on said aligning, and wherein determining the position of the inspection data is performed using the offset and the positions of the alignment sites in the die image space.

55. The system of claim 46, wherein the processor is further configured for generating a context map from the stored high resolution die image, and wherein the context map comprises values for one or more attributes of the stored high resolution die image across the die image space.

56. The system of claim 46, wherein the processor is further configured for acquiring information for a hot spot at one location on the wafer, identifying other locations of the hot spot on the wafer based on the information for the hot spot, and generating care areas for the wafer based on the hot spots at the one location and the other locations.

57. The system of claim 46, wherein the processor is further configured for detecting defects on the wafer based on the inspection data and classifying at least one of the defects based on the position of the inspection data corresponding to the at least one defect in the die image space and a context map, and wherein the context map comprises values for one or more attributes of the stored high resolution die image across the die image space.

58. The system of claim 46, wherein the processor is further configured for generating a context map from the stored high resolution die image, wherein the context map comprises values for one or more attributes of the stored high resolution die image across the die image space and context codes for the values, and wherein the processor is further configured for detecting defects on the wafer based on the inspection data and assigning one of the context codes to at least one of the defects based on the position of the inspection data corresponding to the least one defect in the die image space and the context map.

59. The system of claim 46, wherein the processor is further configured for selecting the predetermined alignment sites based on information about one or more optical modes and pixel size to be used by the inspection system for inspection of the wafer.

60. The system of claim 46, wherein the data acquired for the alignment sites on the wafer and the inspection data are acquired with two or more optical modes on the inspection system.

61. The system of claim 60, wherein the alignment sites used for a first of the two or more optical modes are different from the alignment sites used for a second of the two or more optical modes.

62. The system of claim 60, wherein the data for the predetermined alignment sites used for a first of the two or more optical modes is different than the data for the predetermined alignment sites used for a second of the two or more optical modes.

63. The system of claim 46, wherein the processor is further configured for aligning the data for the alignment sites, determining the positions of the alignment sites, and determining the position of the inspection data during inspection of the wafer.

64. The system of claim 46, wherein the data for the alignment sites on the wafer comprises scanned images, and wherein the data for the predetermined alignment sites comprises high resolution image data from the stored high resolution die image.

65. The system of claim 46, wherein the data for the alignment sites on the wafer comprises scanned images, and wherein the data for the predetermined alignment sites comprises image clips.

66. The system of claim 46, wherein the processor is further configured for selecting the predetermined alignment sites from the stored high resolution die image for the wafer such that there is at least one predetermined alignment site in each of multiple swaths of the inspection data.

67. The system of claim 46, wherein said aligning is performed before defect detection for the wafer.

68. The system of claim 46, wherein setup of aligning the data for the alignment sites, determining the positions of the alignment sites, and determining the position of the inspection data is performed off-tool.

69. The system of claim 46, wherein setup of aligning the data for the alignment sites, determining the positions of the alignment sites, and determining the position of the inspection data is performed on-tool.

70. The system of claim 46, wherein the processor is further configured for selecting the predetermined alignment sites by dividing the stored high resolution die image into portions that correspond to each of multiple swaths of the inspection data and searching the stored high resolution die image to identify and select at least one of the predetermined alignment sites in each of the multiple swaths.

71. The system of claim 46, wherein the processor is further configured for extracting high resolution die image clips for the predetermined alignment sites from the stored high resolution die image and storing the extracted die image clips in a file that is used for inspection of the wafer.

72. The system of claim 46, wherein the processor is further configured for selecting the predetermined alignment sites by pre-processing the stored high resolution die image to select predetermined alignment sites that are compatible with the inspection system and an inspection process to be used for the wafer.

73. The system of claim 46, wherein the processor is further configured for selecting the predetermined alignment sites by scanning a die row on a wafer using the inspection system and processing each frame of a die to identify unique alignment sites.

74. The system of claim 46, wherein the processor is further configured for scanning the wafer using the best imaging mode of the inspection system for inspection to select suitable predetermined alignment sites and determining positions of the selected predetermined alignment sites based on images produced by said scanning and the stored high resolution die image.

75. The system of claim 46, wherein the alignment sites comprise more than one alignment site in each of multiple swaths of the inspection data.

76. The system of claim 46, wherein the alignment sites comprise more than one alignment site in each of multiple swaths of the inspection data to correct scaling errors.

77. The system of claim 46, wherein the predetermined alignment sites are selected at a predetermined frequency across a die on the wafer.

78. The system of claim 46, wherein the predetermined alignment sites are distributed over a die on the wafer at a predetermined minimum interval distance.

79. The system of claim 46, wherein the processor is further configured for aligning the inspection system to the alignment sites to correct stage positional accuracy, rotational errors, x and y translational errors, scaling errors, or some combination thereof in the inspection system.

80. The system of claim 46, wherein the processor is further configured for selecting the predetermined alignment sites to include a set of alignment features that in combination provide sufficient alignment information for said determining the positions of the alignment sites.

81. The system of claim 46, wherein the inspection system is configured to use a bright field mode for inspection of the wafer.

82. The system of claim 46, wherein the inspection system is configured to use a dark field mode for inspection of the wafer.

83. The system of claim 46, wherein the inspection system is configured to use an electron beam imaging mode for inspection of the wafer.

84. The system of claim 46, wherein the processor is further configured for determining a sensitivity for detecting defects on different portions of the wafer based on the position of the inspection data in the die image space, one or more attributes of the stored high resolution die image in the die image space, and one or more attributes of the inspection data, and wherein the one or more attributes of the inspection data comprise one or more image noise attributes, if one or more defects were detected in the different portions, or some combination thereof.

85. The system of claim 84, wherein the one or more attributes of the stored high resolution die image are selected based on yield criticality of defects previously detected in the different portions, fault probability of the defects previously detected in the different portions, or some combination thereof.

86. The system of claim 46, wherein the processor is further configured for determining a sensitivity for detecting defects on different portions of the wafer based on the position of the inspection data in the die image space and a context map, and wherein the context map comprises values for one or more attributes of the stored high resolution die image across the die image space.

87. The system of claim 46, wherein the inspection data comprises data for defects on the wafer, and wherein the processor is further configured for determining positions of the defects in the die image space based on the position of the inspection data in the die image space, determining if the defects are nuisance defects based on the positions of the defects in the die image space and one or more attributes of the stored high resolution die image in the die image space, and determining if the defects not determined to be nuisance defects are systematic or random defects based on the one or more attributes of the stored high resolution die image in the die image space.

88. The system of claim 46, wherein the wafer and additional wafers are processed using wafer level process parameter modulation, and wherein the processor is further configured for detecting defects on the wafer and the additional wafers by comparing inspection data for die on the wafer and the additional wafers to a common standard reference die.

89. The system of claim 46, wherein the data for the alignment sites that is aligned comprises data in each of multiple swaths of the inspection data acquired by the inspection system for the wafer, wherein the alignment sites comprise at least one alignment site in each of the multiple swaths, wherein determining the positions of the alignment sites comprises determining the positions of the at least one alignment site in each of the multiple swaths in the die image space based on the predetermined positions of the predetermined alignment sites in the die image space, and wherein determining the position of the inspection data comprises determining the position of the inspection data in each of the multiple swaths in the die image space based on the positions of the at least one alignment site in each of the multiple swaths in the die image space.

\* \* \* \* \*